United States Patent
Li

(10) Patent No.: US 10,426,411 B2
(45) Date of Patent: Oct. 1, 2019

(54) SYSTEM AND METHOD FOR PROVIDING A REAL-TIME SIGNAL SEGMENTATION AND FIDUCIAL POINTS ALIGNMENT FRAMEWORK

(71) Applicant: Samsung Electronics Co., Ltd., Suwon-si (KR)

(72) Inventor: Yelei Li, Santa Clara, CA (US)

(73) Assignee: Samsung Electronics Co., Ltd. (KR)

( * ) Notice: Subject to any disclaimer, the term of this patent is extended or adjusted under 35 U.S.C. 154(b) by 431 days.

(21) Appl. No.: 15/264,333

(22) Filed: Sep. 13, 2016

(65) Prior Publication Data

US 2018/0000426 A1    Jan. 4, 2018

Related U.S. Application Data

(60) Provisional application No. 62/356,164, filed on Jun. 29, 2016.

(51) Int. Cl.
| | |
|---|---|
| A61B 5/00 | (2006.01) |
| A61B 5/021 | (2006.01) |
| A61B 5/024 | (2006.01) |
| A61B 5/0402 | (2006.01) |
| A61B 5/053 | (2006.01) |

(Continued)

(52) U.S. Cl.
CPC .......... *A61B 5/7278* (2013.01); *A61B 5/0022* (2013.01); *A61B 5/021* (2013.01); *A61B 5/02405* (2013.01); *A61B 5/02416* (2013.01); *A61B 5/0402* (2013.01); *A61B 5/0456* (2013.01); *A61B 5/0533* (2013.01); *A61B 5/0816* (2013.01); *A61B 5/1102* (2013.01); *A61B 5/4818* (2013.01); *A61B 5/681* (2013.01); *A61B 5/721* (2013.01); *A61B 5/725* (2013.01); *A61B 5/7246* (2013.01); *A61B 5/7264* (2013.01); *A61B 5/7282* (2013.01); *A61B 5/742* (2013.01); *A61B 5/01* (2013.01); *A61B 5/02055* (2013.01); *A61B 5/4812* (2013.01); *A61B 5/6823* (2013.01); *A61B 5/6824* (2013.01);

(Continued)

(58) Field of Classification Search
CPC .................................................. A61B 5/7278
USPC ............................................................ 702/127
See application file for complete search history.

(56) References Cited

U.S. PATENT DOCUMENTS

| | | | |
|---|---|---|---|
| 8,137,283 | B2 | 3/2012 | Syeda-Mahmood et al. |
| 8,140,330 | B2 | 3/2012 | Cevik et al. |

(Continued)

OTHER PUBLICATIONS

Schmidt, M., Two-Dimensional Warping for One-Dimensional Signals—Conceptual Framework and Application to ECG Processing, IEEE Transactions on Signal Processing Year: 2014, vol. 62, Issue: 21.

(Continued)

*Primary Examiner* — Hien D Khuu
(74) *Attorney, Agent, or Firm* — McAndrews, Held & Malloy, Ltd.

(57) ABSTRACT

Provided is an electronic device to monitor a user's biological measurements, where a sensor is configured to acquire a first signal from a user, and a diagnostic processor is configured to pre-process the first signal to generate a second signal, segment the second signal to form signal segments, determine at least one event location for each of the signal segments, match adjacent signal segments for feature alignment, and provide a third signal using results of the feature alignment.

25 Claims, 11 Drawing Sheets

(51) Int. Cl.
*A61B 5/08* (2006.01)
*A61B 5/11* (2006.01)
*A61B 5/0456* (2006.01)
*A61B 5/01* (2006.01)
*A61B 5/0205* (2006.01)

(52) U.S. Cl.
CPC ..... *A61B 5/6828* (2013.01); *A61B 2562/0219* (2013.01)

(56) References Cited

U.S. PATENT DOCUMENTS

| | | | |
|---|---|---|---|
| 8,935,195 B2 | 1/2015 | Precup et al. | |
| 2010/0094147 A1* | 4/2010 | Inan | A61B 5/7207 600/500 |
| 2011/0218950 A1 | 9/2011 | Mirowski et al. | |
| 2012/0123232 A1* | 5/2012 | Najarian | A61B 5/0022 600/345 |
| 2012/0123279 A1* | 5/2012 | Brueser | A61B 5/1102 600/481 |
| 2015/0112606 A1* | 4/2015 | He | A61B 5/0285 702/19 |
| 2016/0278644 A1* | 9/2016 | He | A61B 5/02125 |

OTHER PUBLICATIONS

Castro, D., A Method for Context-Based Adaptive QRS Clustering in Real Time, IEEE Journal of Biomedical and Health Informatics Year: 2015, vol. 19, Issue: 5.

* cited by examiner

SYSTEM AND METHOD FOR PROVIDING A REAL-TIME SIGNAL SEGMENTATION AND FIDUCIAL POINTS ALIGNMENT FRAMEWORK

RELATED APPLICATIONS

This application claims the benefit of the U.S. Provisional Application 62/356,164, filed on Jun. 29, 2016, the disclosure of which is incorporated herein in its entirety by reference. The U.S. application Ser. No. 14/928,072 is incorporated in its entirety by reference.

BACKGROUND OF THE INVENTION

The present disclosure relates to measuring a user's body signals, and more particularly, to a system and method for providing a real-time signal segmentation and fiducial points alignment framework.

As with any portable electronic device, it is desirable for a wearable sensor device that monitors biosignals to accurately detect desired biosignals. However, motions of the user, complexity of detected signals, and noise in the detected signals can make accurate detection of biosignals challenging.

Conventional beat detection methods are typically used to determine health measurements (e.g., heart rate, respiration rate) from various types of measurement sensors. These measurement sensors measure different types of sensor signals such as, for example, ballistocardiography (BCG) signals, photoplethysmogram (PPG) signals, electrocardiogram (ECG) signals, galvanic skin response (GSR) signals, and bio-impedance signals. Such conventional beat detection methods are not able to provide accurate detection performance and reliably identify feature points on a noisy signal.

BRIEF SUMMARY OF THE INVENTION

Provided are a system and method for providing a real-time signal segmentation and fiducial points alignment framework. An exemplary embodiment may include a method for determining a signal type for a first signal received via at least one channel from a user, where the first signal is a biosignal of the user. A second signal is provided from the first signal, and the second signal is segmented to form a first signal segment and a second signal segment.

The first signal segment and the second signal segment are processed, based on the signal type, to determine a fiducial point for each of the first signal segment and the second signal segment. When the signal type is of a first type, a fiducial point is directly determined for each of the first signal segment and the second signal segment. When the signal type is of a second type, a first event location is determined from the first signal segment and the first event location is identified as the fiducial point for the first signal segment.

One or more adjacent points from the second signal segment are matched to the fiducial point for the first signal segment, and one of the adjacent points is selected as a fiducial point for the second signal segment that corresponds to the fiducial point for the first signal segment. A third signal is then generated using the fiducial points.

Another exemplary embodiment may include a non-transitory machine-readable medium storing machine executable instructions that when executed causes a computing system to control operations that determines a signal type for a first signal received via at least one channel from a user. The first signal may be a biosignal of the user. A second signal may be provided from the first signal, where the second signal may be different from the first signal or substantially the same as the first signal. The second signal may be segmented to form a first signal segment and a second signal segment. The first signal segment and the second signal segment may then be processed, based on the signal type, to determine a fiducial point for each of the first signal segment and the second signal segment, and a third signal may be generated using the fiducial points.

Still another exemplary embodiment may include a system comprising at least one sensor configured to acquire a first signal from a user, where the sensor(s) has at least one channel, and the first signal is from one channel of the channel(s). A diagnostic processor may be configured to determine a signal type of the first signal, provide a second signal from the first signal, segment the second signal to form a first signal segment and a second signal segment, and process, based on the signal type, the first signal segment and the second signal segment to determine a fiducial point for each of the first signal segment and the second signal segment.

When the signal type is of a first type, the diagnostic processor may determine a fiducial point for each of the first signal segment and the second signal segment. When the signal type is of a second type, the diagnostic processor may determine a first event location from the first signal segment and identify the first event location as the fiducial point for the first signal segment. The diagnostic processor may then match one or more adjacent points from the second signal segment to the fiducial point for the first signal segment, and select one of the adjacent points as a fiducial point for the second signal segment corresponding to the fiducial point for the first signal segment. A third signal may be generated using the fiducial points.

Another embodiment of the disclosure may be a method comprising receiving a first signal via at least one channel from a user, and providing a second signal based on the first signal. The second signal may be segmented to form a plurality of signal segments, and at least one event location may be determined for each of the plurality of signal segments. At least one event location for adjacent ones of the plurality of signal segments may be matched for feature alignment, and a third signal may be provided using results of the feature alignment.

Some embodiments described were examples with two signal segments, however, the number of signal segments may be more than two.

Additional aspects will be set forth in the description that follows and/or learned by practice of the presented exemplary embodiments.

BRIEF DESCRIPTION OF SEVERAL VIEWS OF THE DRAWINGS

These and/or other aspects will become apparent and more readily appreciated from the following description of the exemplary embodiments, taken in conjunction with the accompanying drawings.

DETAILED DESCRIPTION OF THE INVENTION

Figure 1:
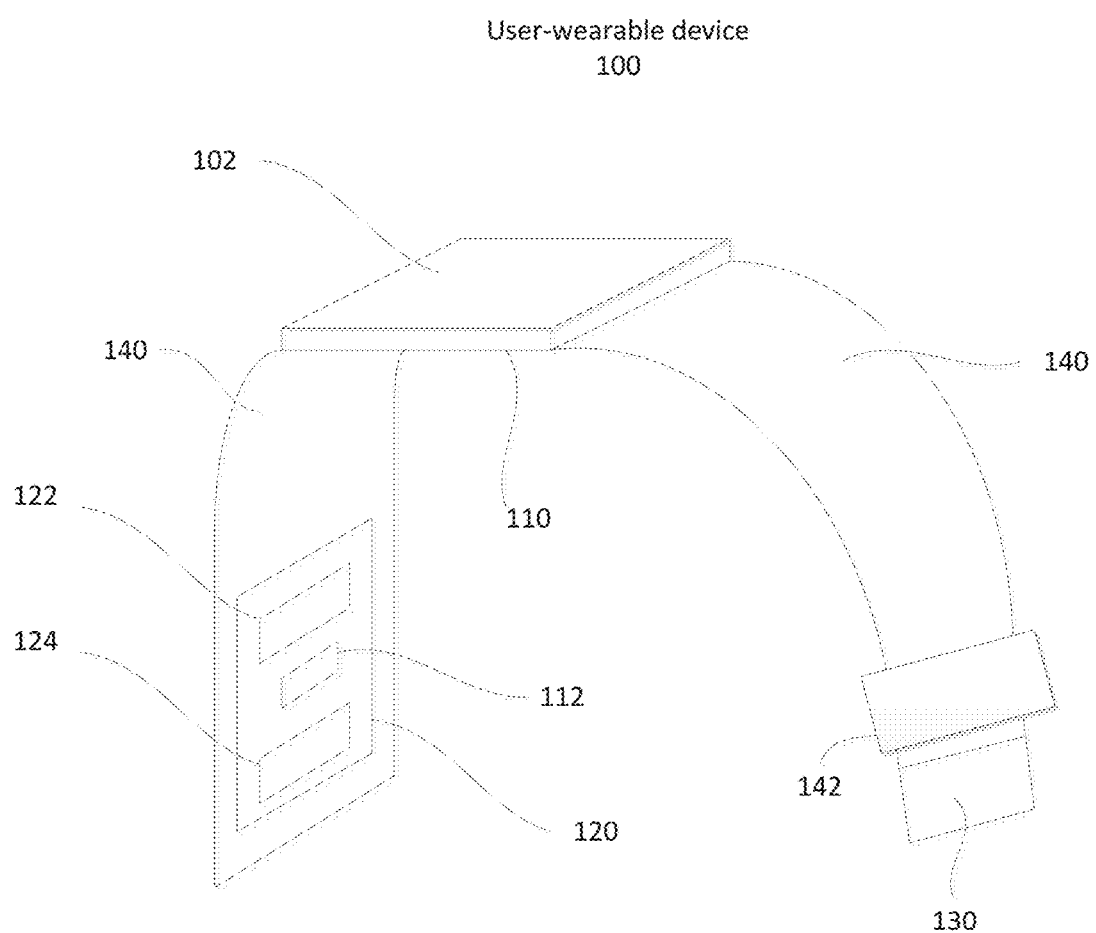
FIG. 1 is a diagram illustrating an electronic device in accordance with an embodiment of the present disclosure.

Advantages and features of one or more embodiments of the present disclosure may be understood more readily by reference to the following detailed description of the embodiments and the accompanying drawings.

In this regard, the present embodiments should not be construed as being limited to the descriptions set forth herein. Rather, these embodiments are provided as examples so that this disclosure will be thorough and complete and will fully convey the concept of the present embodiments to one of ordinary skill in the art. The appended claims illustrate some of the embodiments of the present disclosure.

Like reference numerals refer to like elements throughout the specification. All terms including descriptive or technical terms used herein should be construed as having meanings that are obvious to one of ordinary skill in the art. When a term has an ambiguous meaning due to evolving of language, precedent cases, or the appearance of new technologies, the meaning of a term used in this disclosure should first be clarified by its usage and/or definition in this disclosure. If further clarification is needed, the term should then be clarified as one of ordinary skill in the art would have understood the term in context of the disclosure at the time of the disclosure.

When a part "includes" or "comprises" an element, unless there is a particular description contrary thereto, the part can further include other elements. The term "unit" in the embodiments of the present disclosure means a software component or a hardware component that performs a specific function. The hardware component may include, for example, a field-programmable gate array (FPGA) or an application-specific integrated circuit (ASIC).

Software component may refer to executable code and/or data used by the executable code in an addressable storage medium. Thus, software components may be, for example, object-oriented software components, class components, and task components, and may include processes, functions, attributes, procedures, subroutines, segments of program code, drivers, firmware, micro codes, circuits, data, a database, data structures, tables, arrays, or variables.

A function provided by a "unit" may be divided into additional components and "units."

Reference will now be made in detail to embodiments, examples of which are illustrated in the accompanying drawings. In this regard, the present embodiments may have different forms and should not be construed as being limited to the descriptions set forth herein.

In the following descriptions, well-known functions or constructions are not described in detail so as not to obscure the embodiments with unnecessary detail.

Various embodiments of the present disclosure discloses real-time framework for signal event detection and fiducial points alignment of periodic or pseudo-periodic signals to identify corresponding feature points. The various embodiments include one or more of signal optimization, signal reconstruction, time-delay embedding (TDE) beat detection, and adaptive dynamic time warping (DTW). The various embodiments are robust against morphological variation, high noise level, and/or signal artifacts. Accordingly, various embodiments may be applied to one or more of sleeping/apnea diagnosis, blood pressure diagnosis, heart rate variability (HRV) diagnosis, respiration rate variability (RRV) diagnosis, cardiac arrhythmia detection, and motion recognition.

Various embodiments disclose a real-time signal segmentation and alignment framework for signals with recurrent pattern. The various embodiments may receive and analyze physiological data signal, including, but not limited to, BCG signals (e.g., measured from a low power motion sensor such as an accelerometer), PPG signals (e.g., measured from an optical sensor on a user's wrist), ECG signals (e.g., obtained from a wearable device), GSR signals (e.g., obtained from a GSR sensor), and bio-impedance signals.

FIG. 1 is a diagram illustrating an electronic device in accordance with an embodiment of the present disclosure. Referring to FIG. 1, an electronic device, such as the user-wearable device 100, has a display 102, processors 110 and 112, a sensor module 120, a battery 130, a band 140, and a clasp 142. The sensor module 120 may include sensors 122 and 124. The processor 110, or the CPU 200, or the processor 112 may also be referred to as a diagnostic processor, and may be able to execute instructions. Accordingly, a diagnostic processor may be, for example, a digital signal processor, a controller, a use specific processor, a general processor, and so on. At times, for ease of description, a diagnostic processor may also generally refer to a combination of various hardware (either described above or below).

Although the user-wearable device 100 can be worn on a wrist, various embodiments of the disclosure need not be so limited. The user-wearable device 100 may also be designed to be worn on other parts of the body, such as, for example, on an arm (around the forearm, the elbow, or the upper arm), on a leg, on the chest, on the head like a headband, on the throat like a "choker," and on an ear. The user-wearable device 100 may be able to communicate with other electronic devices such as, for example, a smart phone, a laptop, or various medical devices at a hospital or a doctor's office. This will be described in more detail with respect to FIG. 3.

The display 102 may output monitored physiological signals from the user's body for viewing by the user and/or others. The signals being monitored may be referred to as biosignals or biometric data. The monitored signals may be, for example, heart (pulse) rate, pulse morphology (shape), pulse spacing (inter-beat intervals), respiration (breathing) rate, and blood pressure. The display 102 may also output instructions to the user or others in the use of the user-wearable device 100 or use of other measurement devices, as well as status and diagnostic results, for example.

The processor 110 can receive the monitored signals via a sensor in the sensor module 120. The sensor module 120 may include, for example, the sensors 122 and 124 may acquire signals from the user's wrist when the user-wearable device 100 is worn by a user, as well as provide other information that may indicate the user's body position, motion, and the like. The sensor 122 and/or 124 may be, for example, an accelerometer, an optical sensor, gyrometer, and the like. The processor 112 may control the sensors 122 and 124, and may also process the signals monitored by the sensors 122 and 124. Various embodiments of the disclosure may have the processor 110 also perform the functions of the processor 112. Various embodiments of the disclosure may also have different number of sensors.

The sensor 122 may be, for example, a motion sensor or an accelerometer used to monitor pulse related information. The sensor 124 may be similar to the sensor 122 or a different type of sensor such as, for example, a thermometer for taking the user's temperature. Various embodiments may include different numbers of sensor modules. For example, some embodiments may only have one sensor module, while other embodiments may have 2 or more sensor modules.

The battery 130 is configured to provide power for the user-wearable device 100. The battery 130 may be charged using a wired charging system or a wireless charging system. The band 140 may be wrapped around a wrist and the user-wearable device 100 may be held on the wrist by using the clasp 142.

Figure 2:
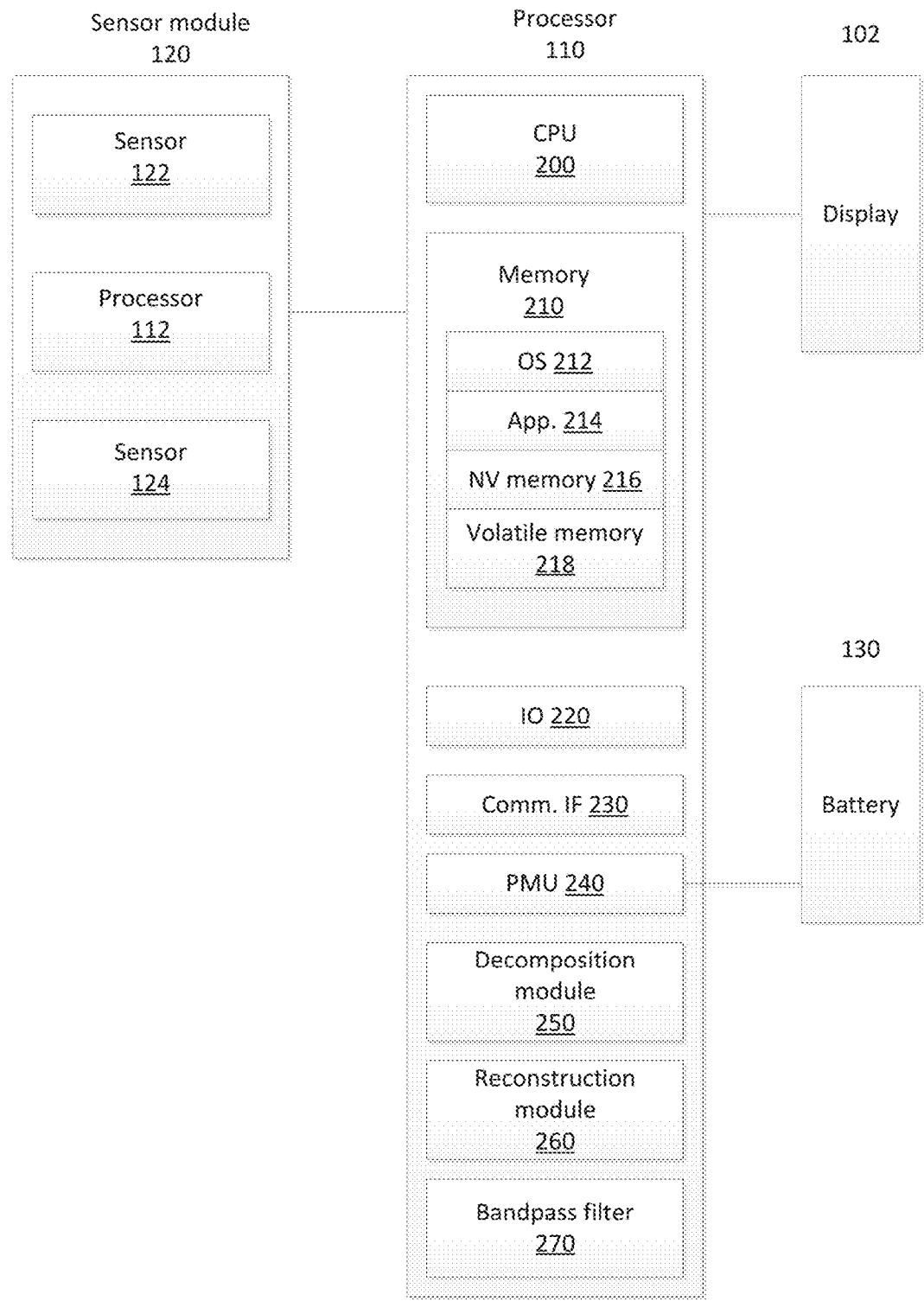
FIG. 2 is a high-level block diagram of an electronic device in accordance with an embodiment of the present disclosure.

FIG. 2 is a high-level block diagram of an electronic device in accordance with an embodiment of the present disclosure. Referring to FIG. 2, there is shown the display 102, the processor 110, the sensor module 120, and the battery 130. Output to the display 102 can be controlled, for example, by the processor 110. The display 102 may also include input devices (not shown) such as, for example, buttons, dials, touch sensitive screen, and microphone.

The processor 110 may include a CPU 200, memory 210, an input/output (IO) interface 220, a communication interface 230, a power management unit (PMU) 240, a decomposition module 250, a reconstruction module 260, and a bandpass filter 270. While the processor 110 is described as including these various devices, other embodiments may use other architectures where the different functionalities are grouped differently. For example, the grouping may be in different integrated circuit chips. Or the grouping may be combining different devices such as the IO interface 220 and the communication interface 230 together, or the decomposition module 250 and the reconstruction module 260 together.

The CPU 200 may control operation of the sensor module 120 as well as receive monitored signals from the sensor module 120. The CPU 200 may control the user-wearable device 100, including processing the monitored signals from the sensor module 120, displaying the processed signals on the display 102, receiving input from the display 102, interfacing with various devices via the IO interface 220 or the communication interface 230 by executing instructions in the memory 210. The IO interface 220 may be used by the CPU 200 to interface with the display 102.

The processor 112 may operate using different architectures in different embodiments. For example, the processor 112 may use the memory 210 to store instructions to execute, or the processor 112 may have its own memory (not shown) for its instructions. Although some embodiments have separate processors 110 and 112, the various embodiments need not be limited so. There may be one processor 110 that controls the functionality of the user-wearable device 100, or there may be multiple processors for the user-wearable device 100.

The memory 210 may include non-volatile memory 216 and volatile memory 218. The operating system and applications may be stored in the non-volatile memory 216. Various embodiments of the disclosure may use different memory architectures that are design and or implementation dependent.

The communication interface 230 may allow the user-wearable device 100 to communicate with other devices via, for example, a wired or wireless protocol such as USB, Bluetooth, Near Field Communication (NFC), and WiFi. The PMU 240 may control receiving power from an outside source, charging the battery 130, as well as allocation of power to the different parts of the user-wearable device 100.

The decomposition module 250 may function to decompose, for example, an input signal such as a BCG signal to multiple frequency bands using time-frequency transforms. The reconstruction module 260 may function to reconstruct, for example, the decomposed signals from the decomposition module 250 to refine and access desired components of the original signal such as the BCG signal. Decomposition and reconstruction of a signal is explained in more detail in the U.S. application Ser. No. 14/928,072, which is incorporated in its entirety by reference. The bandpass filter 270 may be used to select specific frequencies from a signal.

Figure 3:
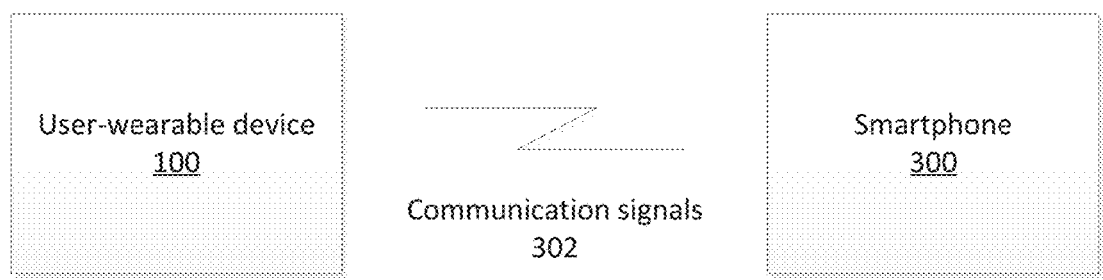
FIG. 3 is an illustration of an electronic device in a communication network in accordance with an embodiment of the present disclosure.

FIG. 3 is an illustration of an electronic device in a communication network in accordance with an embodiment of the present disclosure. Referring to FIG. 3, there is shown the user-wearable device 100 and a smartphone 300. The user-wearable device 100 may communicate with the smartphone 300 using the communication interface 230. The communication may be via the communication signals 302, where the communication may be direct between the user-wearable device 100 and a smartphone 300, or include other elements between the user-wearable device 100 and a smartphone 300.

One of the applications 214 of the user-wearable device 100 may allow the smartphone 300 to control at least some operation of the user-wearable device 100. For example, user-wearable device 100 may output to the display 102 a result of the processing by the processor 110, and/or the same result may be transmitted to the smartphone 300. The user may also select an option either on the user-wearable device 100 or on the smartphone 300. The options may be, for example, to start a biosignal monitoring process by the user-wearable device 100 or to stop the biosignal monitoring process.

Since the smartphone 300 has a larger display, it can be easier for the user to view a result or to select an option on the smartphone 300 rather than on the user-wearable device 100. However, it should be noted that the smartphone 300 may not generally be necessary for operation of the user-wearable device 100.

Figure 4A:
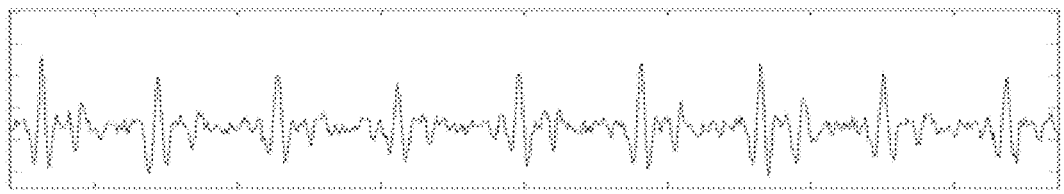
FIG. 4A is an example of a BCG plot in accordance with an embodiment of the present disclosure.
Figure 4B:
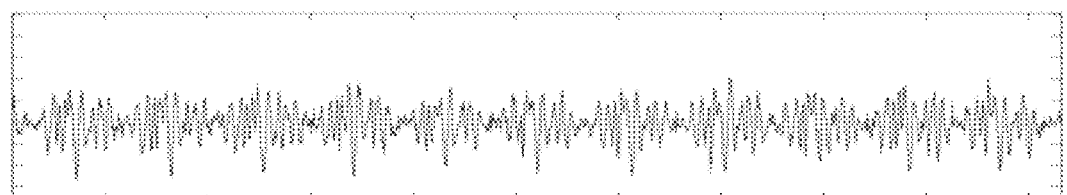
FIG. 4B is an example of a BCG plot in accordance with an embodiment of the present disclosure.
Figure 4C:
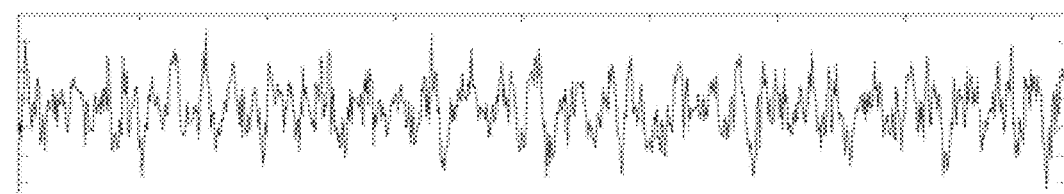
FIG. 4C is an example of a BCG plot in accordance with an embodiment of the present disclosure.
Figure 4D:
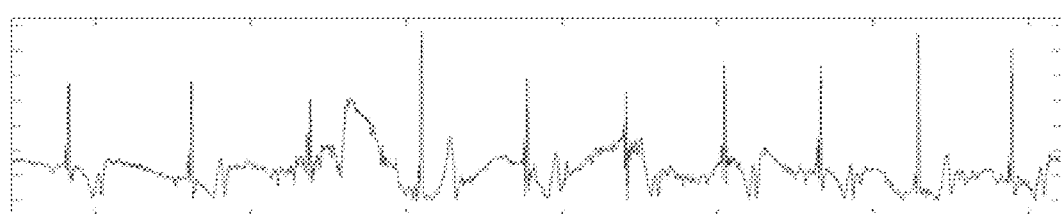
FIG. 4D is an example of an ECG plot in accordance with an embodiment of the present disclosure.
Figure 4E:
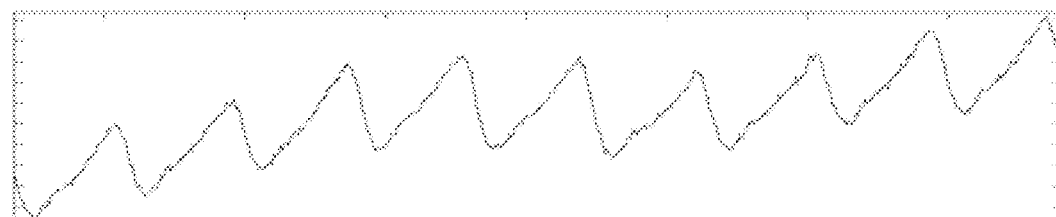
FIG. 4E is an example of a PPG plot in accordance with an embodiment of the present disclosure.

FIGS. 4A-4E illustrates various plots of ECG, BCG, and PPG raw pseudo-periodic signals. FIGS. 4A, 4B, and 4C are examples of BCG plots, FIG. 4D is an example of an ECG plots, and FIG. 4E is an example of a PPG plot. As can be seen, there is a wide range of signal complexity of the pseudo-periodic signals. Various embodiments of the present disclosure are described below for event detection methods that provide reliable accuracy for these signals.

Figure 5:
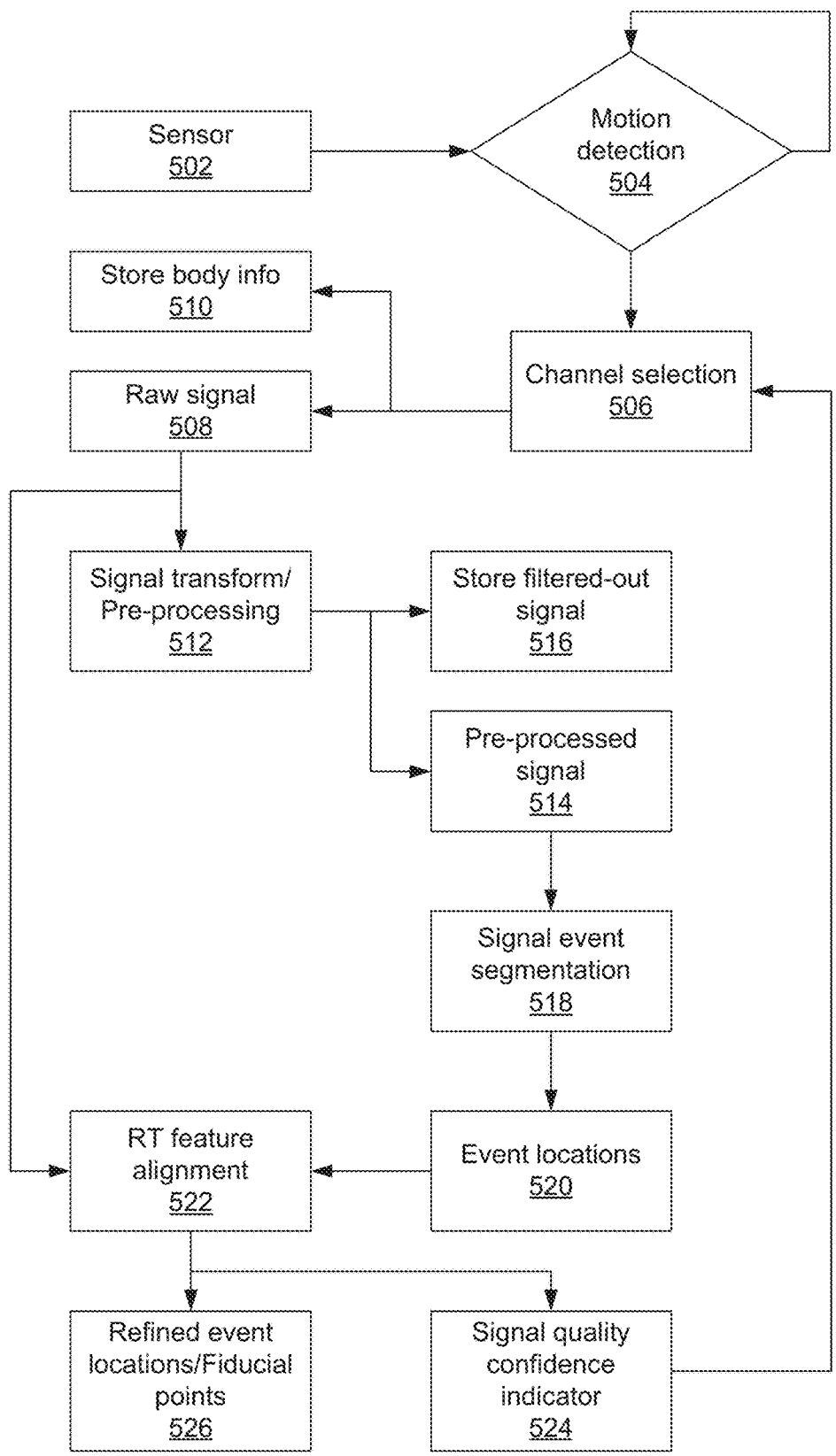
FIG. 5 is an example flow chart for processing an input signal in accordance with an embodiment of the present disclosure.

FIG. 5 is an example flow chart for processing an input signal in accordance with an embodiment of the present disclosure. Referring to FIG. 5, there is shown the flow chart 500 that describes processing signal segmentation and fiducial point detection by a present example system. The signal to be processed may be received from a wearable device such as, for example, a user-wearable device 100. The user-wearable device 100 may detect the biosignals via the sensor module 120.

At 502, if there is more than one sensor, the present example system may select a sensor for biosignal monitoring. The sensor selected may depend on, for example, the clarity of signals, the type of biosignal desired, the power needed to monitor the biosignal, among other criteria. Different criteria may be used for different embodiments. Different sensors may provide different signal types, where the signal type may generally be listed as a first signal type that provides "clean" signals and a second signal type that provides "noisy" signals. "Noisy" signals may need to be pre-processed to remove undesired signal components prior to further processing. For example, ECG and PPG signals may be referred to as the first signal type ("clean") and BCG may be referred to as a second signal type ("noisy"). This is explained further with respect to 512.

At 504, a sensor such as an accelerometer on the sensor module 120 may monitor/detect user motion. While some biosignals may not be affected by user motion, other monitored biosignals provide better signals when the user is substantially stationary. For example, BCG and PPG signals may provide more reliable signals when the user is substantially stationary. Accordingly, when a BCG or PPG signal is desired, if user motion is at or above a pre-determined threshold level, the process may loop back to 504. When the user motion is below the pre-determined threshold, the biosignal from the sensor may be accepted for processing, and the process proceeds to 506. It should be noted that monitoring motion at 504 may be optional for some embodiments of the present disclosure.

At 506, for those embodiments where there are multiple channels to choose from, the present example system may select a channel to determine a desired signal candidate. For example, if measurement sensors such as an accelerometer and a gyrometer provide BCG signals, the channel candidates may include outputs for each of the three axes of the accelerometer, a magnitude of the accelerometer, and multiple outputs for the gyrometer for a multitude of channels from which to pick a channel. However, various embodiments of the disclosure need not be so limited. According to one embodiment, the present example system may further combine channels as signal fusion for signal quality enhancement purposes to form a new channel, further increasing the number of channels. The present example system may select a channel based on, for example, one or more of recurrence rate analysis, determinism of dominate (or dominant) frequency in frequency spectrum, and entropy analysis. For example, when using spectral analysis for BCG channel selection, a higher power ratio of dominant frequency component can indicate better determinism of measured signal as well as fewer artifacts. Various embodiments may also have channel selection as an option. For example, if there is only one channel input, then there is no need for channel selection.

At 508, the present example system receives raw signal from the selected channel of the sensor. At 510, the present example system may store body position information such as posture and orientation of body, for example, in memory 210 to be used for re-initialization of the framework.

At 512, the present example system pre-processes the raw signal (from 508) from the selected channel or directly from the measurement sensor, depending on whether there is a channel selection process at 506. For example, the present example system may pre-process the BCG signals to remove respiration artifacts and high frequency disturbances by using techniques such as, for example, time-frequency processing technique and/or a time-domain processing technique. Time-frequency processing technique includes, among others, wavelet coefficient reconstruction, and time-domain processing technique includes, among others, bandpass filtering.

An embodiment may filter raw BCG signal using a bandpass filter with a desired pass frequency band of, for example, substantially 0.5-3.5 Hz. The bandpass filtering may be via the bandpass filter 270, or performed via digital signal processing using one or more diagnostic processors such as, for example, the processor 112 or the CPU 200. Pre-processing at 512 may also be optional if the signal from the user is determined to be a relatively clean signal. Accordingly, the type of sensor may also be used to determine whether pre-processing is needed. For example, signals from a ECG sensor or a PPG sensor may not need to be pre-processed. Other embodiments may determine whether a signal is clean enough that it does not need to be pre-processed irrespective of the sensor used. Similarly, various embodiments may determine that a signal needs to be pre-processed even when a sensor is used that typically generates a clean signal.

At 514, the present example system generates the pre-processed signals such as, for example, bandpass filtered signals. In other embodiments, the present example system may decompose the raw BCG signals into frequency bands. For example, a BCG signal may be decomposed with a sampling rate of 100 Hz using 5-level Daubechies5 wavelet. The wavelet coefficients from the second to the fifth frequency bands may be considered to carry a majority of the heart beat information. Very low frequency (VLF) bands may be considered as respiration signals. It should be noted that the mother wavelet and decomposition settings (e.g., number of decomposition levels) may be adjusted to achieve similar results without deviating from the scope of the present disclosure.

The present example system may then use wavelet coefficient reconstruction to reconstruct the decomposed BCG signal by applying energy entropy to the decomposed signal frequency bands. The reconstructed BCG signal can then have enhanced fundamental recurrent patterns without harmonic components and artifact ambiguities. The reconstructed BCG signal is shown as the pre-processed signal at 514. While an embodiment of the disclosure can use energy entropy to reconstruct the decomposed BCG signals, the various embodiments of the disclosure need not be so limited. Other techniques can also be used for reconstructing the decomposed BCG signals.

U.S. patent application Ser. No. 15/168,531 titled "Method and Apparatus for Heart Rate and Respiration Rate Estimation Using Low Power Sensor" filed on May 31, 2016 describes a system and method for decomposing a BCG signal into multiple frequency bands and reconstructing the BCG signal, and is incorporated by reference herein.

At 516, present example system may receive filtered-out frequency components from 512, and store the filtered-out frequency components, for example, in memory 210 for further analysis. The present example system may analyze the filtered-out low frequency components to estimate, for example, respiration rate as well as inspiration and expiration onsets. The filtered-out high frequency components may be used, for example, for biometric recognition.

At 518, the present example system may further process the pre-processed signals for signal event segmentation based on, for example, time delay embedding (TDE) beat detection. The TDE approach can produce robust beat locations for different morphological variations of a given signal with low computational cost. The TDE approach maps a signal into a two-dimensional space by plotting sample points against delayed points. Adaptive thresholding beat detection may also be used for signal event segmentation. This is explained further with respect to FIGS. 6A-8.

At 520, the present example system may process the segmented signals for event locations, and real-time feature alignment may take place at 522 using raw signals (from 508). The process from 518 to 522 is described in more detail in the U.S. patent application Ser. No. 14/928,072 titled "Method for Low-Power-Consumption, Robust Estimation of Cardiovascular Periodicity, Contour Analysis, and Heart Rate" filed on Oct. 30, 2015, where the application describes a system and method for time-delay based beat detection, and is incorporated by reference in its entirety herein.

Various similarity matching techniques may be used for real time feature alignment, such as, for example, a correlation method and/or dynamic time warping (DTW) method. For example, DTW may be used to match temporal similarity patterns of two consecutive clipped segments. The DTW distance provides an indicator of similarity for determining an optimal match between two given sequences.

According to one embodiment, a probability function may be applied to the DTW method to assign greater weights of principal feature points near the middle of a segment and assign lesser weights to edge points that could be interpreted as noise. This may further improve reliability and accuracy of alignment performance. This is illustrated with respect to FIG. 9. The probability function includes, but is not limited to, a softmax function, entropy, and modulus distance.

At 524, the present example system may use the output from real-time feature alignment of 522 to determine a signal quality confidence indicator. The alignment level from DTW can be used as confidence indication of signal quality. For example, alignment level may be the ratio of the length of aligned signal to the length of the shorter segment of two pre-aligned signals that are aligned to generate the aligned signal. A higher alignment level indicates that two consecutive segments have higher similarity while a lower alignment level means the signal has larger morphological variation. If the signal quality confidence indicator is below a pre-determined threshold, the process may proceed to 506 for channel selection, and result in re-initialization at 510.

At 526, the present example system can generate refined event locations/fiducial points from raw signals (from 508) and/or the output of the real-time feature alignment (from 522) for use, for example, in sleeping diagnosis, blood pressure diagnosis, heart rate variability (HRV) diagnosis, respiration rate variability (RRV) diagnosis, arrhythmia identification/apnea, and motion recognition, heart (pulse) rate, pulse morphology (shape), pulse spacing (inter-beat intervals), respiration (breathing) rate, and blood pressure.

While an embodiment was described in the flowchart of FIG. 5, it should be understood that various embodiments may use different processes that may show a different flow, add functions, or remove functions. For example, various embodiments may optionally perform the alignment at 522 depending on the type of signal received from the sensor at 502. If the signal received at 502 is via, for example, a PPG or ECG sensor, then there may not be a need for feature alignment. Accordingly, an event location for a segment may be determined independently of other segments and this event may be the fiduciary point for that segment. However, if the signal received at 502 is via, for example, a BCG sensor, then feature alignment may be performed at 522 as described to determine the fiduciary point for each segment. In either case, an output signal can be generated from the determined fiduciary points.

Various embodiments of the disclosure may also use, for example, local minima or local maxima for determining event locations and/or fiducial points.

FIGS. 6A-6E show examples of various plots that are segmented in accordance with an embodiment of the present disclosure. Referring to FIGS. 6A-6E, which correspond to the signal plots shown in FIGS. 4A-4E, each of the signal plots have been segmented as shown by the dashed lines. The segmentation may be a result of, for example, process that took place at 518 of FIG. 5.

Figure 6A:
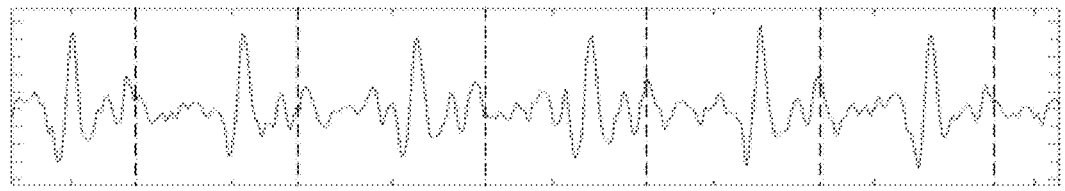
FIG. 6A is an example of a BCG plot that is segmented in accordance with an embodiment of the present disclosure.
Figure 6B:
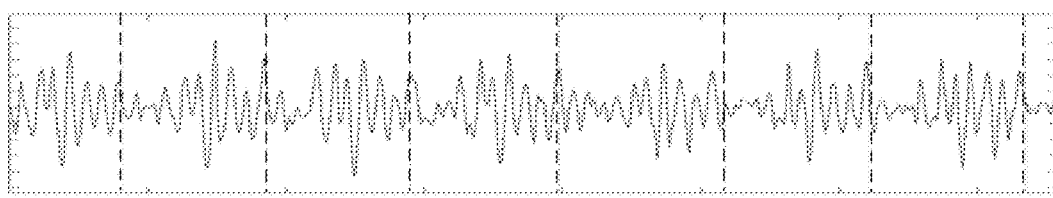
FIG. 6B is an example of a BCG plot that is segmented in accordance with an embodiment of the present disclosure.
Figure 6C:
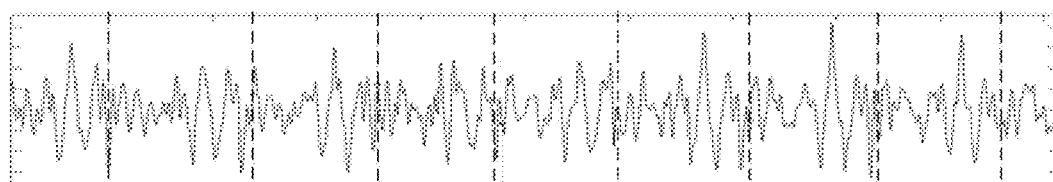
FIG. 6C is an example of a BCG plot that is segmented in accordance with an embodiment of the present disclosure.
Figure 6D:
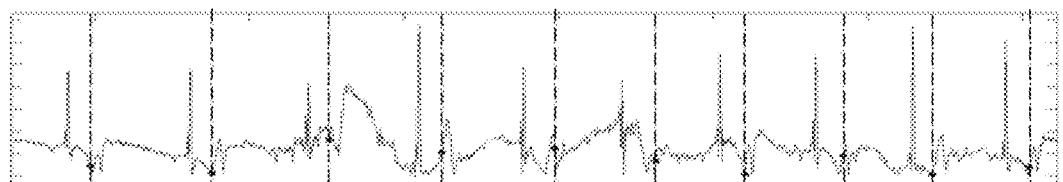
FIG. 6D is an example of an ECG plot that is segmented in accordance with an embodiment of the present disclosure.
Figure 6E:
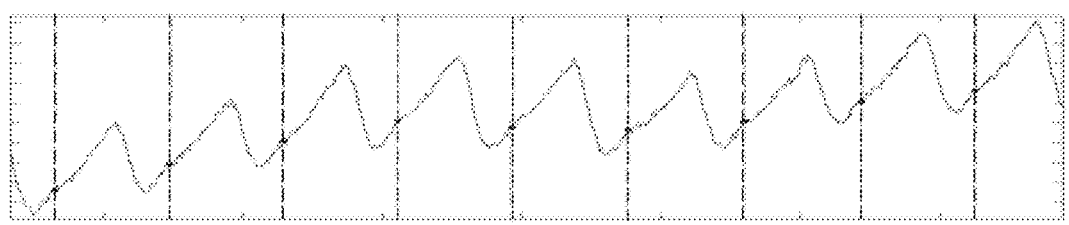
FIG. 6E is an example of a PPG plot that is segmented in accordance with an embodiment of the present disclosure.

FIGS. 6A-6C are BCG waveforms with signal segmentation results using TDE beat detection for various signal sources. FIG. 6D is an ECG waveform with signal segmentation results using TDE beat detection. FIG. 6E is a PPG waveform with signal segmentation results using TDE beat detection. In another embodiment, signal event segmentation (e.g., for BCG signals) may be performed by using adaptive thresholding beat detection approaches. The signals may be further clipped into segments using TDE beat locations (as shown by the dashed lines in FIG. 6A-6E) for the subsequent step.

Figure 7:
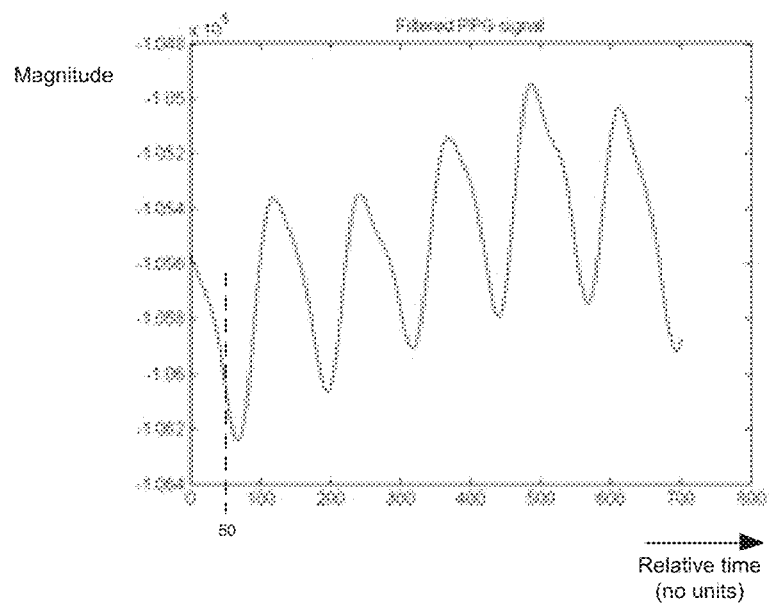
FIG. 7 is an example of a filtered PPG waveform in accordance with an embodiment of the present disclosure.

FIG. 7 illustrates an exemplary waveform of a filtered PPG signal, according to one embodiment. The filtered PPG signal may be for example, a result of process at 514 in FIG. 5.

Figure 8:
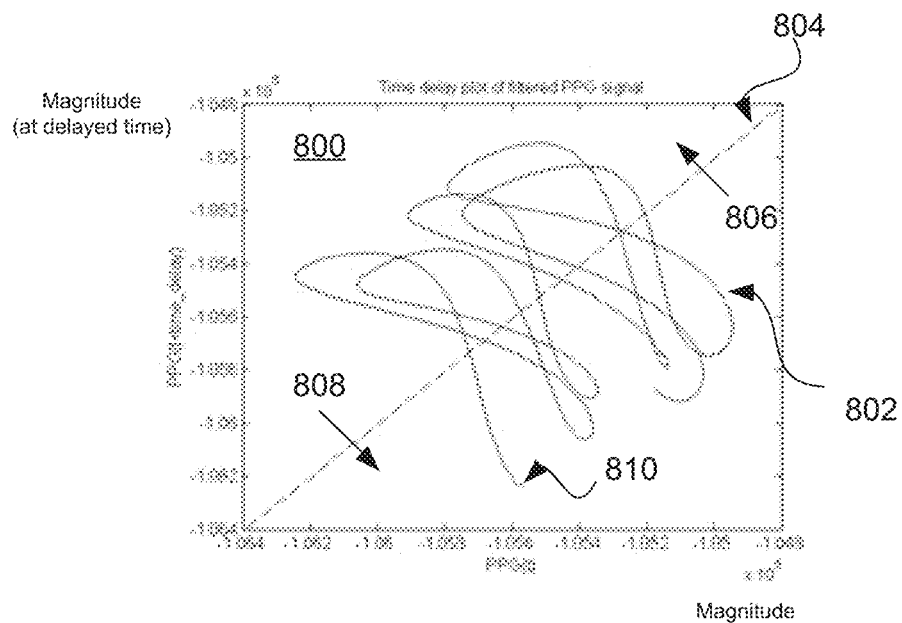
FIG. 8 is an example of a waveform of a time delayed plot for a filtered PPG waveform in accordance with an embodiment of the present disclosure.

FIG. 8 illustrates an exemplary waveform of a time delay plot of the filtered PPG signal, according to one embodiment. A decision line 804 (as indicated by the dashed diagonal line in FIG. 8) is used to identify crossing points.

The crossing points are TDE segmentation locations (event locations) as shown by the dashed lines in FIG. 6.

FIG. 8 illustrates a graphical plot of an exemplary two-dimensional reconstruction of the phase trajectory corresponding to a time series of observational data in accordance with an embodiment. An exemplary trace 800 illustrates several cycles of a two-dimensional reconstruction. The trajectory of the vector 802 with respect to the x-axis and the y-axis is evaluated for crossings at the decision line 804, or ray, passing through the coordinate space origin (0, 0) at a 45-degree angle. The vector 802 crosses a desired decision line 804 at several points along the decision line 804. The arrows 806 and 808 indicate the direction of the orbit. Each time the vector 802 crosses the decision line 804 in a particular direction (for example, from left to right in FIG. 8) indicates the start of a cycle, or period. For the two-dimensional reconstruction, the desired line is of one dimension.

As an example, in FIG. 7, the magnitude at X=0 is $-1.056 \times 10^5$, and the magnitude at relative time 50 is $-1.062 \times 10^5$. For simplicity, we will leave out the exponents to say that the relative magnitude at X=0 is $-1.056$ and the magnitude at relative time 50 is $-1.062$. This can be mapped to FIG. 8, where the point 810 at the end of the trace 800 has the coordinates ($-1.056$, $-1.062$). The trace 800 of FIG. 8 can be plotted by using as X coordinates the magnitudes of the PPG signal at times T along the X axis and using as Y coordinates the magnitudes for the PPG signal at a delayed times T+D, where the relative delay D is 50 in this example.

Figure 9:
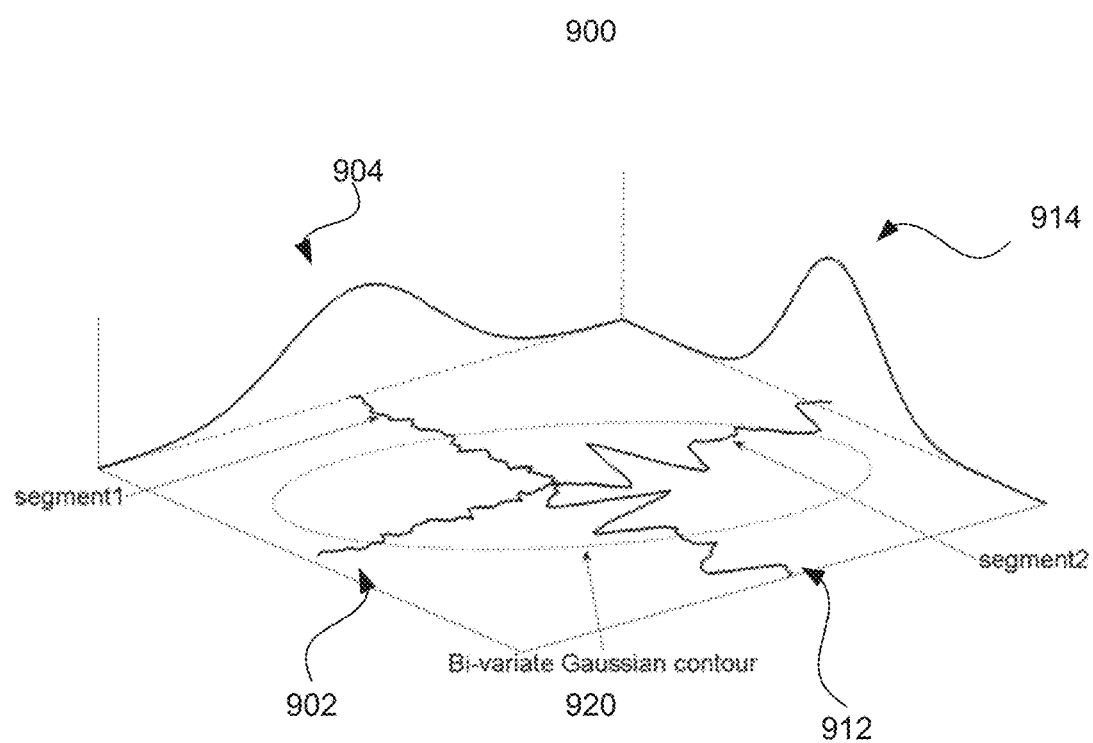
FIG. 9 is an example of a diagram for a bi-variate Gaussian based dynamic time warping (DTW) contour in accordance with an embodiment of the present disclosure.

FIG. 9 illustrates an exemplary diagram for bi-variate Gaussian based DTW contour. A bi-variate distribution may be applied to the DTW matrix. Referring to FIG. 9, there are shown the two segments 902 and 912 that are to be compared. The Gaussian curves 904 and 914 show the portions of the segments 902 and 912, respectively, that should be weighed more heavily for comparisons. As can be seen, the central parts can be weighed more heavily and the end parts can be weighed less heavily. The bi-variate Gaussian contour 920 shows the area of interest with respect to the two segments 902 and 912.

Figure 10A:
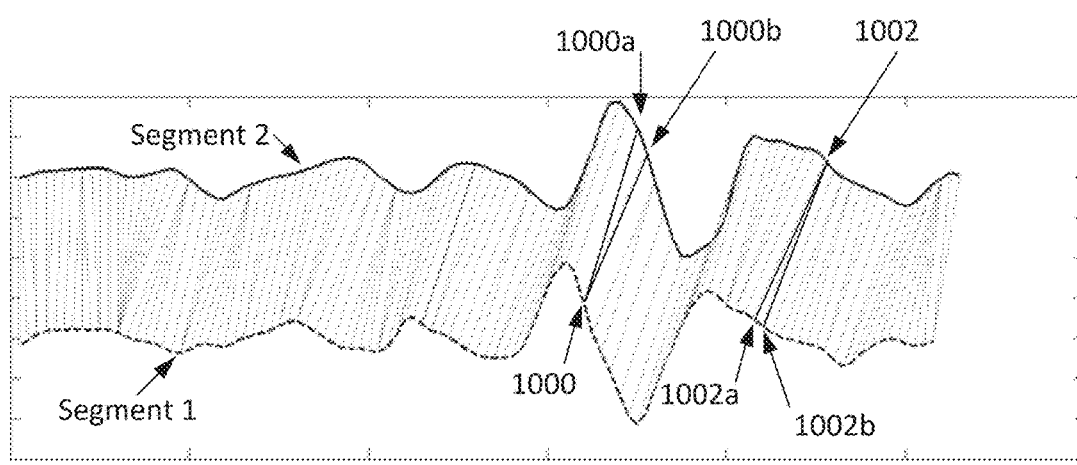
FIG. 10A is an example diagram illustrating point by point matching for a BCG waveform in accordance with an embodiment of the present disclosure.
Figure 10B:
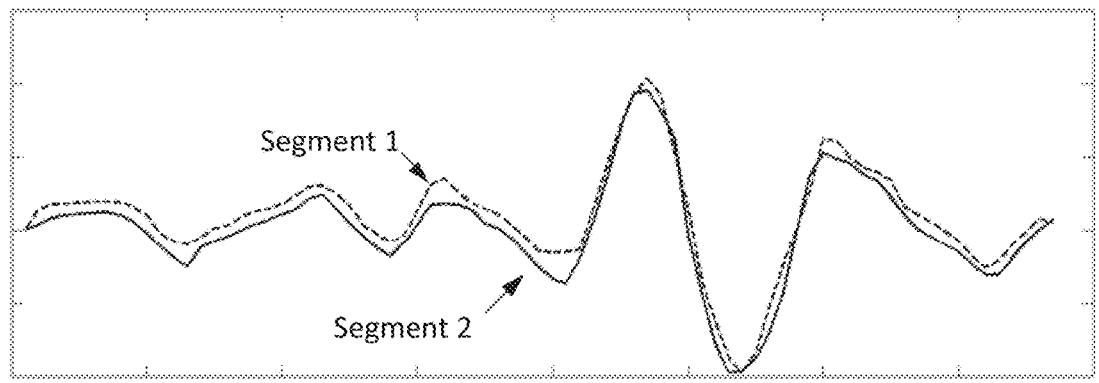
FIG. 10B is an example diagram illustrating BCG matching comparison with residual points removed in accordance with an embodiment of the present disclosure.

FIGS. 10A and 10B illustrate exemplary waveforms for BCG segment matching results, according to one embodiment.

FIG. 10A is an example diagram illustrating point by point matching for a BCG waveform in accordance with an embodiment of the present disclosure. FIG. 10A illustrates one example of DTW graphical performance on two consecutive BCG segments using the present DTW method where salient features, especially systolic waveforms, are correctly identified pairwise, and edging residual sections show mismatching. Referring to FIG. 10A, there are shown segment 1 and segment 2, where various points of segments 1 and 2 are matched to each other. One point on a segment may match to multiple points on the other segment. For example, the point 1000 on segment 1 may match to points 1000a and 1000b on segment 2. While various embodiments may have different methods for selecting one point from the plurality of matching points, one method to use may be to keep the point that is the closest. Accordingly, for point 1000 on segment 1 the point 1000b on segment 2 may be kept as the matching point. Similarly, the point 1002 on segment 2 may be matched to point 1002a on segment 1. The non-selected points are referred to as residual points and may be discarded.

FIG. 10B is an example diagram illustrating BCG matching comparison with residual points removed in accordance with an embodiment of the present disclosure. Referring to FIG. 10B, there is shown BCG matching comparison with residual points removal for segments 1 and 2. The two segments are truncated to the same length by removing residual points. Various embodiments may use beat by beat matching results for applications such as, for example, heart beat arrhythmia detection, heart rate variability, and blood pressure calculation.

Figure 11A:
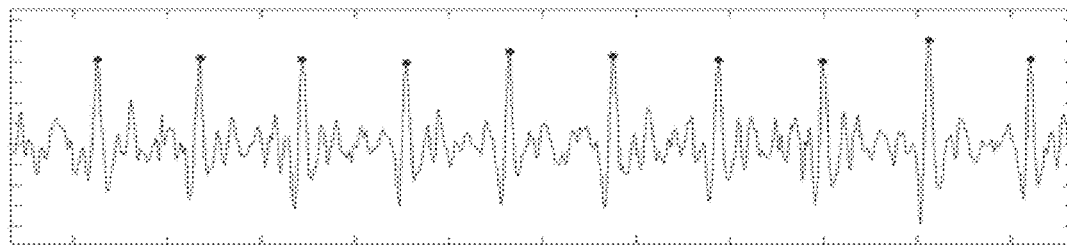
FIG. 11A illustrates feature points of a BCG plot in accordance with an embodiment of the present disclosure.
Figure 11B:
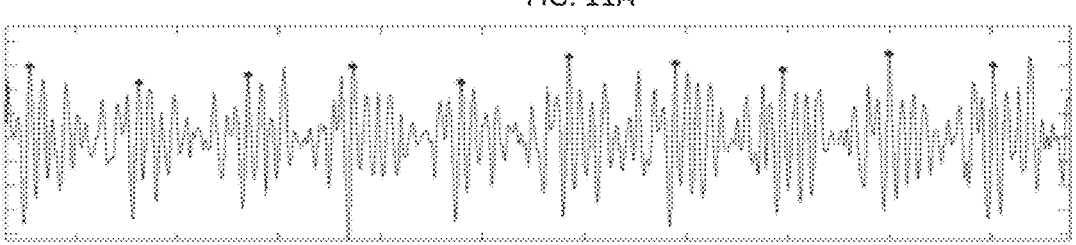
FIG. 11B illustrates feature points of a BCG plot in accordance with an embodiment of the present disclosure.
Figure 11C:
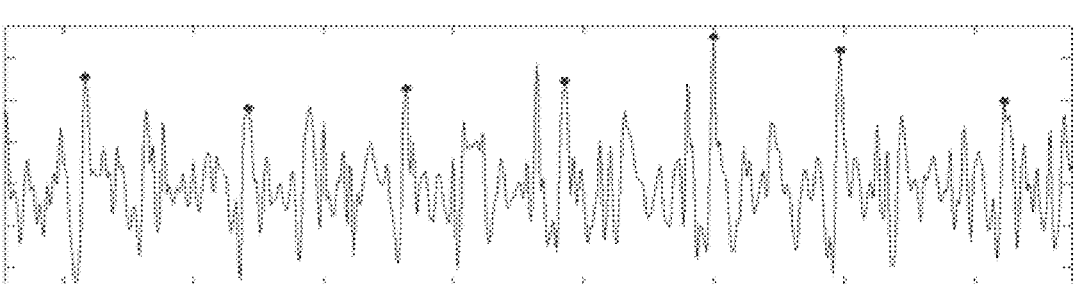
FIG. 11C illustrates feature points of a BCG plot in accordance with an embodiment of the present disclosure.
Figure 11D:
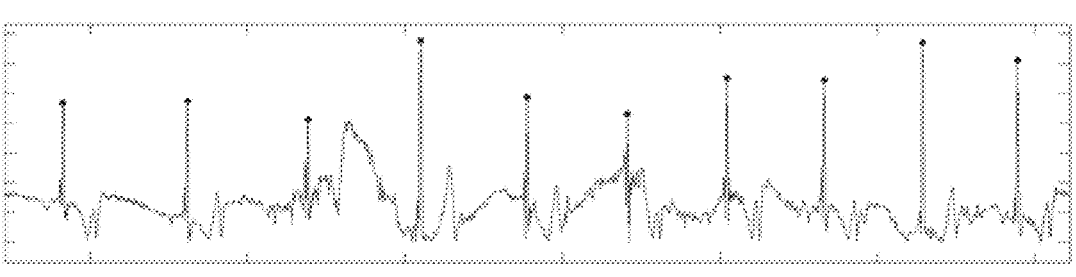
FIG. 11D illustrates feature points of an ECG plot in accordance with an embodiment of the present disclosure.
Figure 11E:
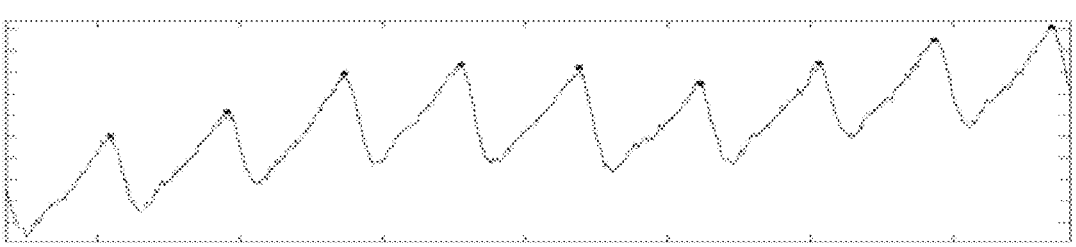
FIG. 11E illustrates feature points of a PPG plot in accordance with an embodiment of the present disclosure.

FIGS. 11A-11E illustrate feature points of various plots in accordance with an embodiment of the present disclosure. FIGS. 11A-11C illustrate feature points for BCG signals, FIG. 11D illustrates feature points for an ECG signal, and FIG. 11E illustrates feature points for a PPG signal. The feature points (e.g., J peak or I peak from a BCG signal, R peaks from an ECG signal, and primary peaks on PPG signal) are determined by finding the point of local maxima energy for the first segment after initialization or reset. The corresponding feature points for following segments may be identified using the present DTW method.

According to one embodiment, other fiducial points can be selected for the first segment similarly after initialization or reset. Fiducial points of following segments can then be iteratively identified. For example, if the primary foot on PPG is selected as feature point for the first event, the present framework can identify corresponding primary peaks in following PPG segments.

Figure 12:
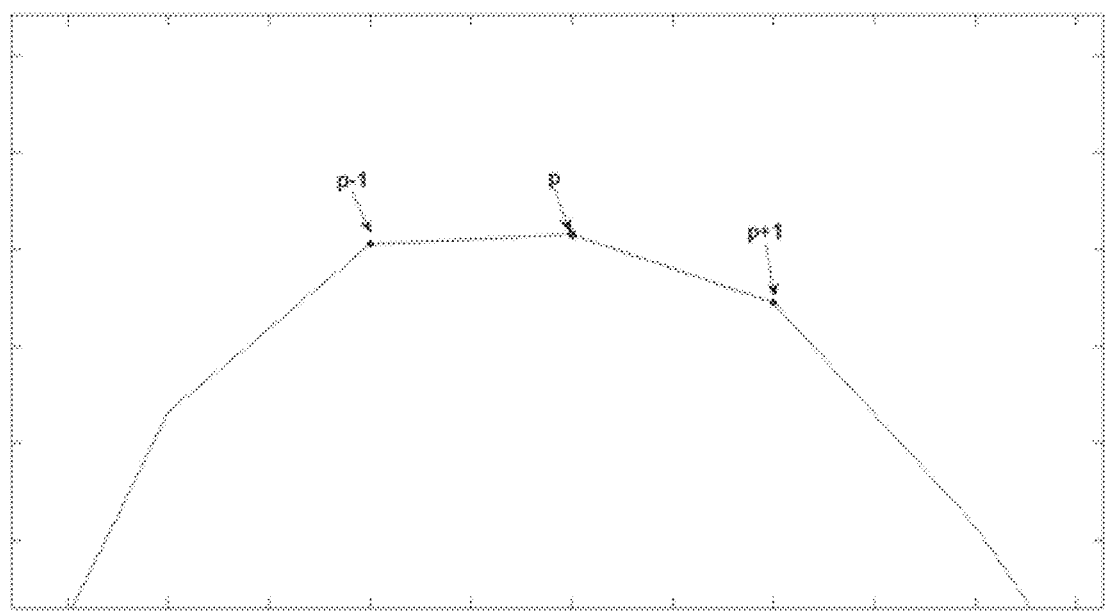
FIG. 12 is an example waveform for beat location interpolation in accordance with an embodiment of the present disclosure.

FIG. 12 is an example waveform for beat location interpolation in accordance with an embodiment of the present disclosure. Due to the limitation of the sensor sampling rate, beat detection precision is of scale 1/Fs as shown in FIG. 12, where Fs is the sampling frequency. According to one embodiment, the present example system further provides interpolation to increase the resolution of the beat location beyond the original sampling rate.

In one embodiment, a more accurate beat location and amplitude can be derived from following equations:

$$\text{Amplitude} = \sqrt{\text{Amplitude}_p^2 + 0.8467 * (\text{Amplitude}_{p-1} + \text{Amplitude}_{p+1})^2} \quad (1)$$

$$\text{Shift ratio} = \sqrt{\left|\frac{\text{Amplitude}_{p+1} - \text{Amplitude}_{p-1}}{\text{Amplitude}_p}\right|} * \text{sign}\left(\frac{\text{Amplitude}_{p+1} - \text{Amplitude}_{p-1}}{\text{Amplitude}_p}\right) * 0.602 \quad (2)$$

where $\text{Amplitude}_{p-1}$, $\text{Amplitude}_p$, $\text{Amplitude}_{p+1}$ are the amplitudes of three adjacent points and the middle point P is selected as the feature point. The "Shift ratio" is the horizontal adjustment of the middle point P with respect to a percent of the length of the segment it is in. It is appreciated that the present example system may use any type of interpolation method without deviating from the scope of the present disclosure. For example, the interpolation methods can include higher order polynomial interpolation, linear interpolation, as well as others.

According to one embodiment, beat and fiducial point detection is initialized when an enable stream is triggered. For example, beat information may be continuously calculated when user activity level is under a pre-determined threshold as described regarding motion detection in FIG. 5. Once the user activity level crosses the pre-determined threshold, the present example system resets beat and fiducial point detection based on a reset flag. According to one embodiment, in a wearable device application, the present example system records a position/orientation estimation along with the reset flag. The position estimation provides valuable gestural information of measured subject especially for sleeping data.

According to one embodiment, the present example system may combine position information with beats and fiducial locations for other diagnosis applications, such as sleeping staging, heart rate variability (HRV) diagnosis, and sleeping position diagnosis.

Various embodiments have described processing BCG, ECG, and PPG signals. However, it should be realized that various embodiments of the present disclosure apply to other biosignals as well.

Various embodiments of the disclosure may be written as computer programs and may be implemented in general-use digital computers that execute the programs using a non-transitory computer-readable recording medium.

Non-transitory computer-readable recording medium may include, for example, magnetic storage media (e.g., ROM, floppy disks, and hard disks), and optical recording media (e.g., CD-ROMs, or DVDs).

While various embodiments of the disclosure have been described with reference to the figures, it will be understood by those of ordinary skill in the art that various changes in form and details may be made therein without departing from the spirit and scope of the disclosure as defined by the following claims. Accordingly, the above embodiments and all aspects thereof are examples only and are not limiting.

What is claimed:

1. A method comprising:
   determining a signal type for a first signal received via at least one channel from a user;
   monitoring motion of the user, wherein when the monitored motion is below a pre-determined threshold:
   providing a second signal from the first signal;
   segmenting the second signal to form a first signal segment and a second signal segment;
   processing, based on the signal type, the first signal segment and the second signal segment to determine a fiducial point for each of the first signal segment and the second signal segment,
   wherein
   when the signal type of the first signal is determined to be a ballistocardiography (BCG) signal:
   determining a first event location from the first signal segment and identifying the first event location as the fiducial point for the first signal segment,
   matching one or more adjacent points from the second signal segment to the fiducial point for the first signal segment,
   selecting one of the one or more adjacent points as a fiducial point for the second signal segment corresponding to the fiducial point for the first signal segment, and
   generating a third signal using the fiducial points.

2. The method of claim 1, wherein the fiducial point is determined for each of the first signal segment and the second signal segment by determining one of a local maximum and a local minimum.

3. The method of claim 1, wherein:
   when the first signal is determined to be an electrocardiogram (ECG) signal or a photoplethysmogram (PPG) signal, the first signal bypasses pre-processing, and, therefore, the second signal provided is the same as the first signal, and
   when the first signal is determined to be a BCG signal the second signal is provided by pre-processing the first signal with one of time-domain processing and time-frequency processing.

4. The method of claim 3, wherein time-domain processing comprises bandpass filtering.

5. The method of claim 3, wherein the time-frequency processing comprises wavelets coefficient reconstruction.

6. The method of claim 1, comprising finalizing a selection of one of the at least one channel for receiving the first signal.

7. The method of claim 1, comprising storing portions of the first signal.

8. The method of claim 1, comprising using one of time delay embedding (TDE) beat detection and adaptive thresholding to form the first signal segment and the second signal segment.

9. The method of claim 1, comprising using a similarity matching technique for matching the first signal segment and the second signal segment.

10. The method of claim 9, wherein the similarity matching technique comprises at least one of dynamic time warping (DTW) method and correlation method.

11. The method of claim 10, comprising applying a probability function to the DTW method to assign different weights to portions of the first signal segment and the second signal segment.

12. The method of claim 1, comprising selecting, if the third signal is below a pre-determined threshold, a new channel for receiving the first signal from the user, wherein any of the at least one channel can be the new channel.

13. A system comprising:
   at least one sensor configured to acquire a first signal from a user, wherein the at least one sensor has at least one channel, and the first signal is from one channel of the at least one channel, and wherein at least one of the at least one sensor is configured to monitor motion of the user; and
   a diagnostic processor configured to:
   when the monitored motion is below a pre-determined threshold:
   determine a signal type of the first signal;
   provide a second signal from the first signal;
   segment the second signal to form a first signal segment and a second signal segment;
   process, based on the signal type, the first signal segment and the second signal segment to determine a fiducial point for each of the first signal segment and the second signal segment,
   wherein when the first signal is determined to be a ballistocardiography (BCG) signal, the diagnostic processor is configured to:
   determine a first event location from the first signal segment and identifying the first event location as the fiducial point for the first signal segment,
   match one or more adjacent points from the second signal segment to the fiducial point for the first signal segment,
   select one of the one or more adjacent points as a fiducial point for the second signal segment corresponding to the fiducial point for the first signal segment, and
   generate a third signal using the fiducial points.

14. The system of claim 13, further comprising memory configured to store at least body position information of the user, wherein the body position information is determined by the diagnostic processor from signals monitored by the at least one sensor.

15. The system of claim 13, wherein the fiducial point is determined for each of the first signal segment and the second signal segment by determining one of a local maximum and a local minimum.

16. The system of claim 13, wherein:
when the first signal is determined to be an electrocardiogram (ECG) signal or a photoplethysmogram (PPG) signal, the diagnostic processor is configured to bypass pre-processing the first signal, and, therefore, provide the second signal that is the same as the first signal, and
when the first signal is determined to be a BCG signal, the diagnostic processor is configured to provide the second signal by pre-processing the first signal with one of time-domain processing and time-frequency processing.

17. The system of claim 16, wherein time-domain processing comprises bandpass filtering.

18. The system of claim 16, wherein the time-frequency processing comprises wavelets coefficient reconstruction.

19. The system of claim 13, wherein the diagnostic processor is configured to finalize a selection of a channel for receiving the first signal from the at least one sensor.

20. The system of claim 13, further comprising memory configured to store at least portions of the first signal.

21. The system of claim 13, wherein the diagnostic processor is configured to use one of time delay embedding (TDE) beat detection and adaptive thresholding to form the first signal segment and the second signal segment.

22. The system of claim 13, wherein the diagnostic processor is configured to use a similarity matching technique for matching the first signal segment and the second signal segment.

23. The system of claim 22, wherein the similarity matching technique comprises at least one of dynamic time warping (DTW) method and correlation method.

24. The system of claim 23, wherein the diagnostic processor is configured to apply a probability function to the DTW method to assign different weights to portions of the first signal segment and the second signal segment.

25. The system of claim 13, wherein the diagnostic processor is configured to select, if the third signal is below a pre-determined threshold, a channel from the at least one sensor for receiving the first signal from the user.

* * * * *